(12) United States Patent
Ichihashi

(10) Patent No.: US 8,641,606 B2
(45) Date of Patent: Feb. 4, 2014

(54) ENDOSCOPE APPARATUS

(76) Inventor: Masaki Ichihashi, Kokubunji (JP)

( * ) Notice: Subject to any disclaimer, the term of this patent is extended or adjusted under 35 U.S.C. 154(b) by 1517 days.

(21) Appl. No.: 12/026,257

(22) Filed: Feb. 5, 2008

(65) Prior Publication Data

US 2009/0198106 A1 Aug. 6, 2009

(51) Int. Cl.
*A61B 1/06* (2006.01)
*A61B 1/04* (2006.01)

(52) U.S. Cl.
USPC ........... 600/178; 600/110; 600/130; 600/175; 600/176; 600/179

(58) Field of Classification Search
USPC ......... 600/101, 109, 110, 129, 130, 112, 118, 600/175–182, 160
See application file for complete search history.

(56) References Cited

U.S. PATENT DOCUMENTS

| | | | | |
|---|---|---|---|---|
| 4,989,586 | A * | 2/1991 | Furukawa | 600/110 |
| 5,876,326 | A * | 3/1999 | Takamura et al. | 600/110 |
| 2005/0182291 | A1* | 8/2005 | Hirata | 600/101 |
| 2006/0183977 | A1* | 8/2006 | Ishigami et al. | 600/179 |
| 2007/0008407 | A1* | 1/2007 | Yamamoto et al. | 348/65 |
| 2007/0191684 | A1* | 8/2007 | Hirata | 600/179 |

FOREIGN PATENT DOCUMENTS

| | | |
|---|---|---|
| JP | 2004-248835 | 9/2004 |
| JP | 2005-323885 | 11/2005 |
| JP | 2005-348846 | 12/2005 |

OTHER PUBLICATIONS

Office Action issued by Japanese Patent Office on Aug. 16, 2011 in connection with corresponding application No. 2006-206404 and English Translation thereof.
Office Action issued by Japanese Patent Office on Dec. 20, 2011 in connection with corresponding application No. 2006-206404.
English translation of claims as originally filed in Japanese Patent application No. 2006-206404.

* cited by examiner

*Primary Examiner* — Philip R Smith
*Assistant Examiner* — Rynae Boler
(74) *Attorney, Agent, or Firm* — Ostrolenk Faber LLP

(57) ABSTRACT

An endoscope apparatus includes: a long insertion portion that is inserted into an examination object; an illumination portion provided at a distal end portion of the insertion portion, that irradiates illumination light at the examination object; an image pickup portion provided inside the distal end portion, that picks up reflected light captured in the insertion portion; and a heat radiating member that radiates heat emitted from at least one of the illumination portion and the image pickup portion. A distal end of the heat radiating member is disposed on a further proximal end side of the insertion portion than a maximum external diameter portion of the image pickup portion within the distal end portion. Therefore, not only can heat be radiated from the distal end portion of the insertion portion, but the distal end portion of the insertion portion can also be formed with a narrow diameter.

23 Claims, 6 Drawing Sheets

ENDOSCOPE APPARATUS

BACKGROUND OF THE INVENTION

1. Field of the Invention

The present invention relates to an endoscope apparatus for observing an object to be examined.

2. Description of the Related Art

In recent years, an endoscope apparatus comprising an insertion portion that is inserted into an object to be examined, an LED provided at a distal end portion of the insertion portion, and a CCD that picks up reflected light from an observation target inside the object to be examined is utilized in various fields such as the medical care field and industrial field.

An LED and a CCD are elements that emit heat. When heat generated from these elements is left as it is, the image quality of the observation image deteriorates and the luminous efficiency of the LED declines, or in some cases a fault arises in the LED or the CCD.

Therefore, for example, Japanese Patent Laid-Open No. 2004-248835 discloses an endoscope having a heat radiating portion configured by disposing an LED adjacent to a distal end side of a long heat-radiating wire element, and passing a proximal end side of the heat radiating wire element through vicinity of the CCD to dispose the heat-radiating wire element towards the proximal end side of an insertion portion. According to the endoscope apparatus disclosed in Japanese Patent Laid-Open No. 2004-248835, by means of this configuration, heat emitted from the LED and CCD can be released at the proximal end side of the insertion portion via the heat radiating wire element.

SUMMARY OF THE INVENTION

An endoscope apparatus relating to the present invention comprises: a long insertion portion that is inserted into an object to be examined; a distal end portion of the insertion portion; an illumination portion that irradiates illumination light at an observation target inside the object to be examined; an image pickup portion that picks up reflected light that is captured in the insertion portion; and a heat radiating member in which a distal end is arranged closer to a proximal end side of the insertion portion than a maximum external diameter portion of the image pickup portion inside the distal end portion.

DETAILED DESCRIPTION OF THE PREFERRED EMBODIMENTS

Hereunder, an endoscope apparatus according to an embodiment of the present invention will be described with reference to the accompanying drawings.

Figure 1:
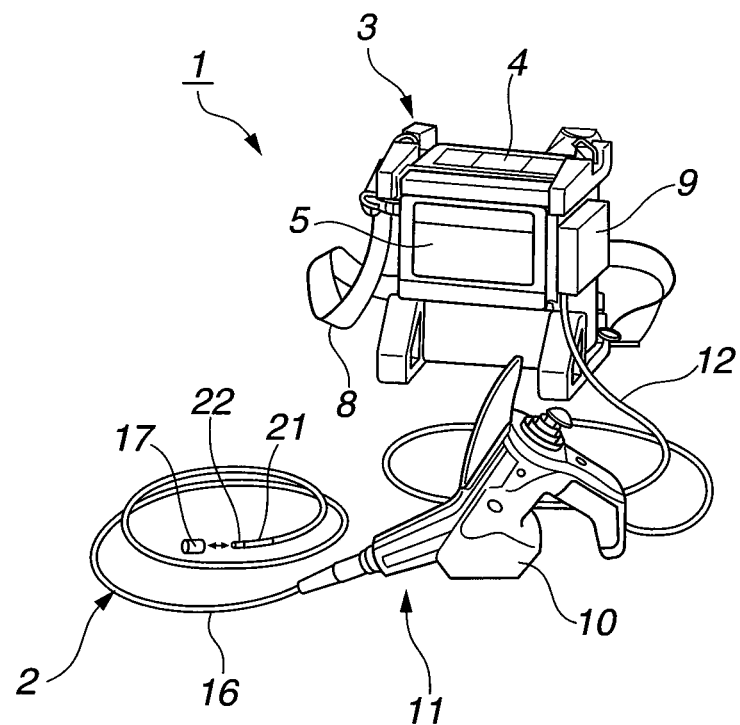
FIG. 1 is an overall configuration diagram that illustrates a first embodiment of the endoscope apparatus according to the present invention.

FIG. 1 is a view showing an endoscope apparatus 1 as an embodiment of the present invention.

The endoscope apparatus 1 comprises a rectangular endoscope main body portion 3 that performs overall control of the endoscope apparatus 1.

On the top surface of the endoscope main body portion 3 is provided a front panel 4 for performing various settings. A monitor 5 such as an LCD for displaying an observation image is attached to the side surface of the endoscope main body portion 3. A belt 8 is attachable to the endoscope main body portion 3 so that a user can hang the endoscope main body portion 3 over a shoulder to perform hands-free operations.

Further, a scope unit 11 is detachably attached to the endoscope main body portion 3.

The scope unit 11 comprises a control unit 10 for performing operations and an insertion portion 2 provided in the control unit 10.

A universal cable 12 is provided in the control unit 10. A scope connector 9 is provided at one end of the universal cable 12. The scope connector 9 is detachably attached to the endoscope main body portion 3.

The insertion portion 2 comprises a long insertion main body portion 16 and an endoscope adapter 17 to be detachably connected to the distal end of the insertion main body portion 16. The endoscope adapter 17 and a distal end cylindrical portion 22, described later, comprise the distal end portion of the insertion portion 2.

The back end of the insertion main body portion 16 is attached to the control unit 10.

A bendable bending portion 21 is arranged in the vicinity of the distal end portion of the insertion main body portion 16. The bending portion 21 is configured so as to be bent in a desired direction by operating the control unit 10. As a result, the distal end of the insertion portion 2 is configured so as to be oriented in a desired direction through the bending portion 21.

Figure 2:
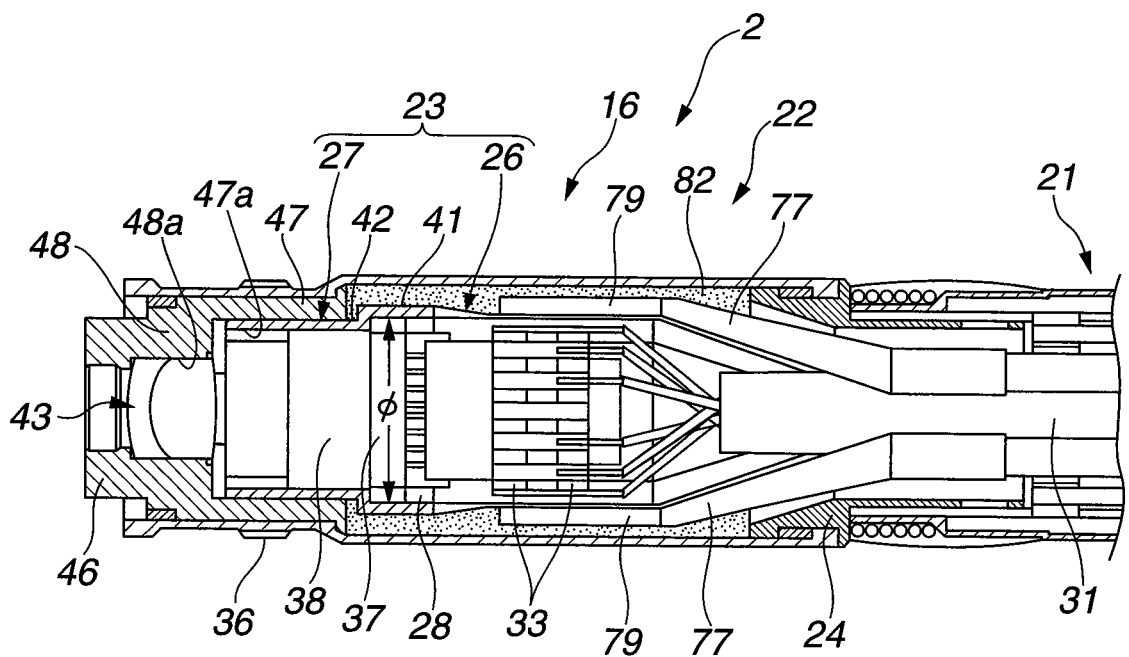
FIG. 2 is a sectional view showing an enlarged view of the distal end portion of the insertion portion shown in FIG. 1, illustrating a state in which the insertion portion is observed from underneath.

As shown in FIG. 2, a distal end cylindrical portion (distal end portion) 22 formed in a cylindrical shape is attached via a substantially tubular connecting member 24 to the distal end of the bending portion 21. Inside the distal end cylindrical portion 22 is provided an image pickup portion 29 for obtaining an observation image of an observation target within an object to be examined. The image pickup portion 23 comprises an image pickup main body portion 26 and a filter portion 27 for obtaining light of an appropriate wavelength.

The image pickup main body portion 26 comprises a CCD substrate 33 and a CCD 28 that photo-electrically convert reflected light from an observation target that is captured inside the distal end cylindrical portion 22. An electric signal from the CCD 28 and CCD substrate 33 is output through a signal wire 31. A cover glass 37 that protects the front surface of the CCD 28 is arranged at the front of the CCD 28 that is the distal end side of the insertion main body portion 16. The CCD 28 and the cover glass 37 are disposed inside a substantially semi-cylindrical image pickup cover 41. The image pickup cover 41 protects the CCD 28 and the cover glass 37. At the front of the cover glass 37 is provided an optical filter 38 for cutting out infrared rays among reflected light from an observation target that is captured inside the distal end cylindrical portion 22. The optical filter 38 is disposed inside a cylindrical filter support frame 42. The optical filter 38 is supported within the distal end cylindrical portion 22 by the filter support frame 42. The above described image pickup cover 41 is provided at the back end of the filter support frame 42. The filter support frame 42 and the image pickup cover 41 are formed in an integrated condition.

At the front of the optical filter 38 is provided a distal end side objective optical system 43 for forming reflected light from an observation target that is captured inside the distal end cylindrical portion 22 into an image on the CCD 28. The distal end side objective optical system 43 is disposed inside a tubular optical support block 46. The optical support block 46 is configured by a greater inner diameter portion 47 that is disposed at the back end side of the distal end cylindrical portion 22 and a lesser inner diameter portion 48 that is disposed on the distal end side and has a smaller diameter than the greater inner diameter portion 47 that are integrally connected. That is, a plurality of cylindrical holes 47a and 48a of differing diameters are formed inside the optical support block 46. The filter support frame 42 is fitted and fixed in the cylindrical hole 47a of the greater inner diameter portion 47 from the back end thereof. The aforementioned distal end side objective optical system 43 is arranged in the cylindrical hole 48a of the lesser inner diameter portion 48. The distal end side objective optical system 43 is supported inside the distal end cylindrical portion 22 by the lesser inner diameter portion 48.

Figure 3:
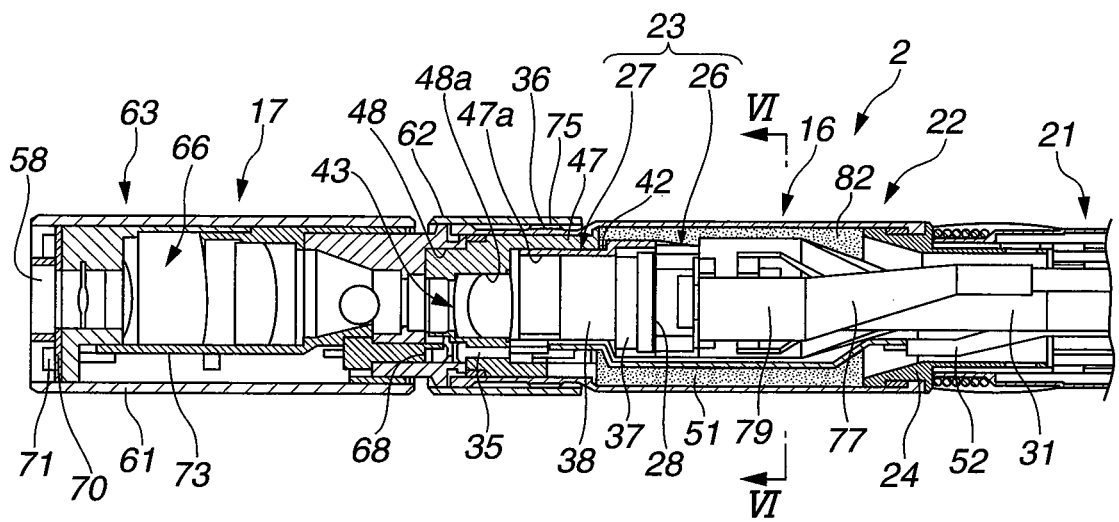
FIG. 3 is a sectional view showing an enlarged view of the distal end portion of the insertion portion shown in FIG. 1, illustrating a state in which the insertion portion is observed from the side.

Next, the configuration of the distal end portion of the insertion portion 2 is described using FIG. 2 and FIG. 3. FIG. 2 is a sectional view for describing the configuration of the distal end side of the insertion main body portion 16. FIG. 3 is a sectional view for describing the configuration of the distal end side of the insertion main body portion 16 in a state in which the endoscope adapter 17 is attached thereto.

As shown in FIG. 3, a pair of distal end side FPCs 51 for supplying power to an LED 71 as an illumination portion, described later, are provided inside the distal end cylindrical portion 22. The back ends of the distal end side FPCs 51 are electrically connected to a lead 52 that is extended through the inside of the insertion main body portion 16 from a power supply portion of the endoscope main body portion 3. The distal ends of the distal end side FPCs 51 are electrically connected to a pair of insertion side electrode portions 35 provided at the distal end of the distal end cylindrical portion 22. The distal ends of the insertion side electrode portions 35 protrude forward from the distal end surface of the distal end cylindrical portion 22.

A male screw portion 36 is formed around the entire circumference of the peripheral surface of the distal end cylindrical portion 22. An endoscope adapter 17 for forward viewing is detachably attached to the distal end portion of the distal end cylindrical portion 22. The endoscope adapter 17 is used for capturing reflected light from an observation target and sending the captured light to the insertion main body portion 16.

The endoscope adapter 17 comprises an attachment hood 62 and an adapter main body portion 63 formed in a substantially cylindrical shape. The adapter main body portion 63 and the attachment hood 62 are disposed on the same axis line and are rotatably connected to each other.

An adapter side objective optical system 66 for adjusting an angle of view, an observation depth, or the brightness or the like is provided inside the adapter main body portion 63. Further, a donut-shaped LED substrate portion 70 is provided at the distal end of the adapter main body portion 63. An LED 71 that irradiates illumination light is provided on the surface of the LED substrate 70.

An observation window 58 for capturing reflected light from an observation target is provided at the distal end of the adapter main body portion 63.

A pair of contact pins 68 made of a conductive member are arranged at a back end part of the adapter main body portion 63. Each contact pin 68 is formed to extend in a rod shape. One end of each contact pin 68 protrudes backward from the back end face of the adapter main body portion 63. The contact pins 68 are electrically connected with the LED 71 via the adapter side FPC 73.

A cylindrical distal end cover 61 is attached to the periphery of the adapter main body portion 63.

Further, a female screw portion 75 that extends across the entire circumference is formed at the back end part of the inner peripheral surface of the aforementioned attachment hood 62.

According to this configuration, when the distal end of the distal end cylindrical portion 22 is inserted from the open end of the attachment hood 62 and the attachment hood 62 is rotated, the female screw portion 75 and the male screw portion 36 engage. Through engagement of the female screw portion 75 and the male screw portion 36, the endoscope adapter 17 is attached to the distal end cylindrical portion 22.

When the endoscope adapter 17 is attached to the distal end cylindrical portion 22, the insertion side electrode portion 35 and the contact pins 68 contact to thereby electrically connect the insertion side electrode portion 35 and the contact pins 68. As a result, power is supplied to the LED 71 from the power supply portion of the endoscope main body portion 3 through the lead 52, the distal end side FPC 51, the insertion side electrode portion 35, the contact pins 68 and the adapter side FPC 73.

Further, according to the present embodiment, a pair of heat radiating wire elements 77 configured by bundling together multiple wire elements made of a high thermal conductivity material such as aluminum are provided inside the insertion portion 2. The distal end of a first end portion of the plurality of heat radiating wire elements 77 that have a first end portion and a second end portion is disposed on the further rear side than the maximum external diameter portion of the image pickup portion 23, i.e. on the proximal end side of the insertion portion 2. In this connection, the term "high thermal conductivity material" refers to a material having a high thermal conductivity exceeding a thermal conductivity of a general-purpose resin or the like (approximately 0.7 W/mK). For example, the thermal conductivity of aluminum is 235 W/mK.

In this case, as shown in FIG. 2, with respect to the external diameter of the image pickup portion 23, in general, the external diameter φ is largest at the section of the image pickup cover 41 protecting the CCD 28 that has a large diameter. That is, according to the present embodiment, the image pickup cover 41 constitutes the maximum external diameter portion of the image pickup portion 23.

Figure 4:
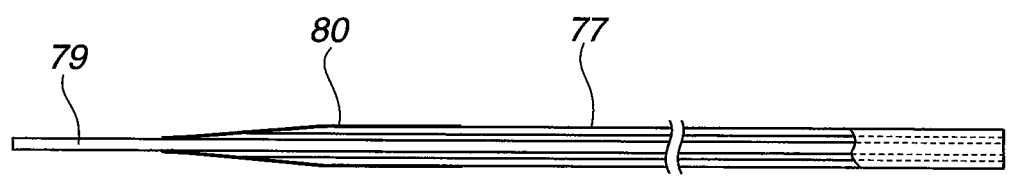
FIG. 4 is a side view illustrating a heat radiating wire element according to the present embodiment.
Figure 5:
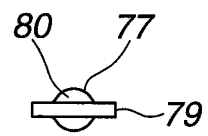
FIG. 5 is a front view showing the heat radiating wire element illustrated in FIG. 4 from the front.

Further, as shown in FIG. 4 and FIG. 5, a broad portion 79 that is made with a wider width than that of the other portions is formed at the first end portion of the heat radiating wire element 77. The broad portion 79 is formed by providing a heat-shrinkable tube at the distal end of the heat radiating wire element 77, applying a solder from the distal end of the heat radiating wire element 77, and then removing the heat-shrinkable tube after the solder hardens. A heat-shrinkable tube 80 made of a member that is shrunk by heating is covered over the proximal end side of the broad portion 79 of the distal end portion of the heat radiating wire element 77.

The second end portion of the heat radiating wire element 77 is also fixed by a solder. In this connection, similarly to above, the second end portion of the heat radiating wire element 77 is also formed by providing a heat-shrinkable tube on the second end portion, applying a solder from the back end of the heat radiating wire element, and removing the heat-shrinkable tube after the solder hardens.

Figure 6:
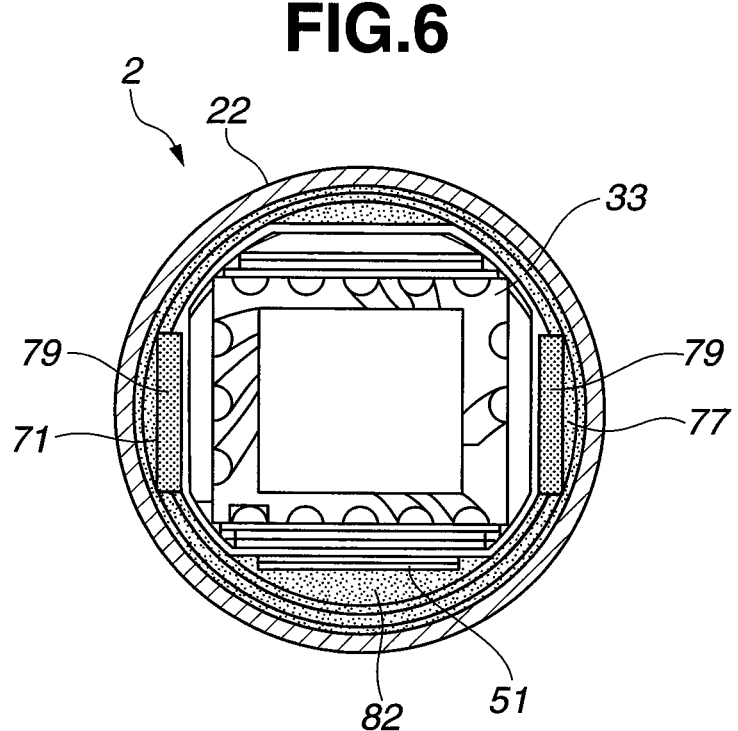
FIG. 6 is a sectional view along the arrowed line VI-VI shown in FIG. 3.

As shown in FIG. 2 and FIG. 6, a pair of broad portions 79 are arranged at both ends in the width direction of the distal end cylindrical portion 22 so as to sandwich the CCD substrate 33 there between. Further, the second end portion of the heat radiating wire element 77 is extended as far as a predetermined position of the insertion main body portion 16.

The length dimensions of the pair of heat radiating wire elements 77 are designed to differ from each other. Therefore, since the first end portions of the heat radiating wire elements 77 are aligned at the same position, the second end portions of the heat radiating wire elements 77 are arranged at mutually different positions. In this case, the term "position" refers to the position in the longitudinal direction of the insertion portion 16. The diametrical dimensions of the second end portions of the heat radiating wire element 77 increase because of the solder, and the second end portions also harden. Therefore, to ensure that the second end portions of the heat radiating wire element 77 do not overlap in the width direction of the insertion portion 2, the second end portions of the heat radiating wire element 77 are disposed at respectively different positions. Thus, not only it is possible to easily perform a work to assemble the heat radiating wire element 77, but a configuration can also be adopted that does not affect a bending operation of the bending portion 21.

In this connection, the term "solder" is a generic name for a brazing alloy with a low melting point, for example, a melting point of 450° C. or less. Brazing alloys include, for example, Pb—Sn alloy, and various compositions are known. In addition, non-lead alloys such as Sn—Ag and Bi—Sn alloys can also be preferably used.

Further, in the present embodiment, the distal end cylindrical portion 22, optical support block 46, distal end cover 61, attachment hood 62, and adapter main body portion 63 comprise a highly thermal conductive member such as SUS, aluminum, or brass.

Further, a sealing element 82 that seals the inside of the distal end cylindrical portion 22 is filled inside the distal end cylindrical portion 22. The sealing element 82 is an adhesive that has a high thermal conductivity that exceeds the thermal conductivity of a normal adhesive (approximately 0.7 W/mK), such as an adhesive in which a metal oxide is filled into silicone rubber. The sealing element 82 fixes the image pickup portion 23, the heat radiating wire elements 77, and the distal end side FPC 51 and the like inside the distal end cylindrical portion 22.

Next, an action of the endoscope apparatus 1 in the present embodiment configured in this manner is described.

First, the endoscope adapter 17 is attached to the distal end of the insertion main body portion 16. Subsequently, when the power supply portion of the endoscope main body portion 3 is driven, the power from the power supply portion is supplied to the LED 71 through various cables and the like so that illumination light is emitted from the LED 71. When the insertion portion 2 is inserted inside an object to be examined in this state, reflected light from the observation target is captured by the endoscope adapter 17 through the observation window 58. The reflected light that is captured forms an image on the CCD 28 inside the distal end cylindrical portion 22 through the adapter side objective optical system 66 and the distal end side objective optical system 43. Output signals from the CCD 28 and the CCD substrate 33 are then sent via the signal wire 31 to a CCU that performs signal processing and are also supplied to the monitor 5. Thereby, an observation image is reflected on the monitor 5, and the user performs a predetermined examination of an observation target while viewing the observation image.

In this case, when the LED 71 and the CCD 28 are driven, heat is emitted from the LED 71 and the CCD 28. If the heat from the LED 71 and the CCD 28 is left as it is, the temperature inside the distal end cylindrical portion 22 will increase and noise will be generated in the observation image.

In the present embodiment, heat from the LED 71 and the CCD 28 is released in the following manner.

That is, heat emitted from the CCD 28 is conveyed to the broad portion 79 of the heat radiating wire element 77, and released to proximal end side of the heat radiating wire element 77.

Further, heat emitted from the LED 71 is conveyed to the adapter main body portion 63 and the distal end cover 61, and further conveyed to the attachment hood 62, the optical support block 46, and the distal end cylindrical portion 22. The heat conveyed from the LED 71 is also conveyed to the broad portion 79 of the heat radiating wire element 77 in the same manner as the aforementioned heat from the CCD 28 and released to the proximal end side of the heat radiating wire element 77.

Thus, according to the endoscope apparatus 1 of the present embodiment, since the distal end of the heat radiating wire element 77 is disposed to the further rear side than the maximum external diameter portion of the image pickup portion 23 and, further, heat emitted from the LED 71 and CCD 28 and the like can be easily conveyed to the proximal end side of the insertion portion 2 through the heat radiating wire element 77, not only can release of heat be performed effectively at the distal end cylindrical portion 22, but furthermore, the distal end cylindrical portion 22 can easily be made with a small diameter.

More specifically, although the distal end portion of the insertion portion 2 must have a diameter of a certain degree of size since it is necessary to locate various components such as the CCD 28 inside the distal end portion of the insertion portion 2, it is required that the overall diameter be as small as possible since the insertion portion 2 is to be inserted into an object to be examined. However, according to the endoscope apparatus disclosed in Japanese Patent Laid-Open No. 2004-248835, there is a problem that a heat radiating wire element is passed through the area in the vicinity of the CCD at which generally the diameter is largest and thus the diameter of the overall distal end portion of the insertion portion increases.

In contrast, according to the endoscope apparatus 1 of the present embodiment in which the distal end of the heat radiating member is disposed on the further proximal end side of the insertion portion than the maximum external diameter portion of the image pickup portion 23 in the distal end portion 2, not only is it possible not to pass a heat radiating member through the periphery of the maximum external diameter portion image pickup portion 23, but it is also possible to easily convey heat emitted from the image pickup portion 23 to the proximal end side of the insertion portion 2 and also to easily make the diameter of the distal end portion of the insertion portion 2 small.

Further, the sealing element 82 that has a high thermal conductivity is provided inside the distal end cylindrical portion 22 in the endoscope apparatus 1. Therefore, heat that is conveyed to the optical support block 46 or the distal end cylindrical portion 22 can be easily conveyed to the heat radiating wire element 77 through the sealing element 82. Thus, the heat release efficiency can be improved.

That is, in the endoscope apparatus 1 relating to the present invention, a sealing element that seals the inside of the distal end portion 2 is provided in the distal end portion 2, and the sealing element has a high thermal conductivity. Thus, in the endoscope apparatus 1, heat that is emitted from at least one of the illumination portion and the image pickup portion 23 is conveyed to a heat radiating member through the distal end portion 2 and the sealing element.

Therefore, in the endoscope apparatus 1, heat that is emitted from at least one of the illumination portion, and the image pickup portion 23 can be easily released with good efficiency.

Further, in the endoscope apparatus 1, since the heat-shrinkable tube 80 is provided in the heat radiating wire elements 77, when the sealing element 82 is filled inside the distal end cylindrical portion 22, the sealing element 82 can be prevented from seeping out to the bending portion 21 side by a capillary phenomenon through each of the wire elements of the heat radiating wire elements 77. It is therefore possible to prevent a situation arising in which it becomes difficult to bend the bending portion 21. Also, since the heat-shrinkable tube 80 is shrunk by heat, it is possible to firmly bundle together the wire elements of the heat radiating wire elements 77 so that the sealing element 82 can be reliably prevented from seeping out.

In this connection, although in the present embodiment the broad portion 79 of the heat radiating wire element 77 is provided at both ends in the width direction of the distal end cylindrical portion 22, taking into account the efficiency of thermal conduction from the distal end cylindrical portion 22 to the broad portion 79, it is preferable to adopt a configuration in which the broad portion 79 is brought as close as possible to the inner surface of the distal end cylindrical portion 22 to bring the broad portion 79 and the inner surface of the distal end cylindrical portion 22 into contact.

Figure 7:
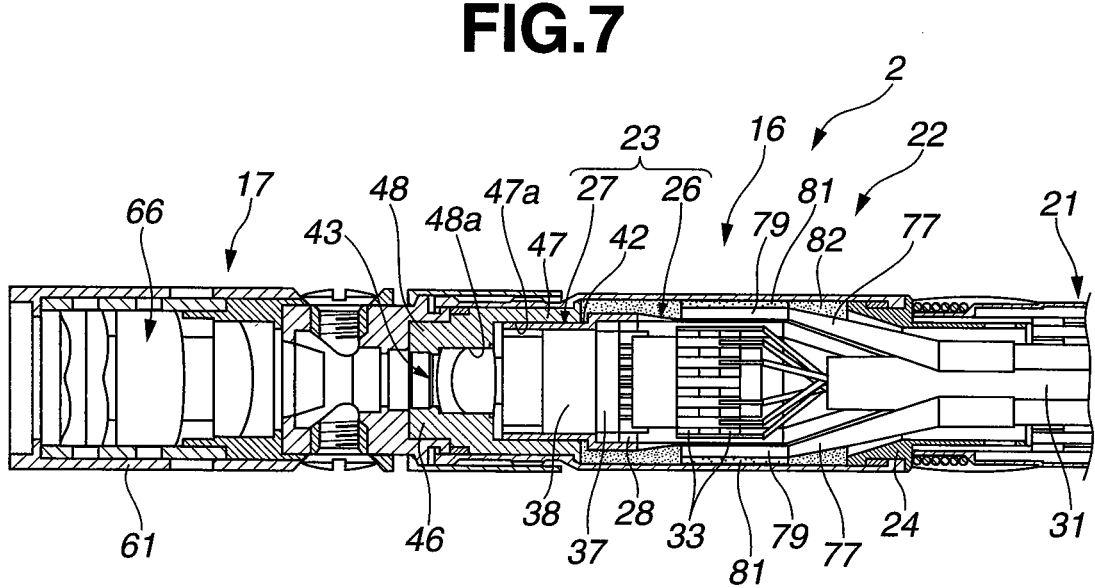
FIG. 7 is a sectional view showing a modified example of the insertion portion shown in FIG. 2.
Figure 8:
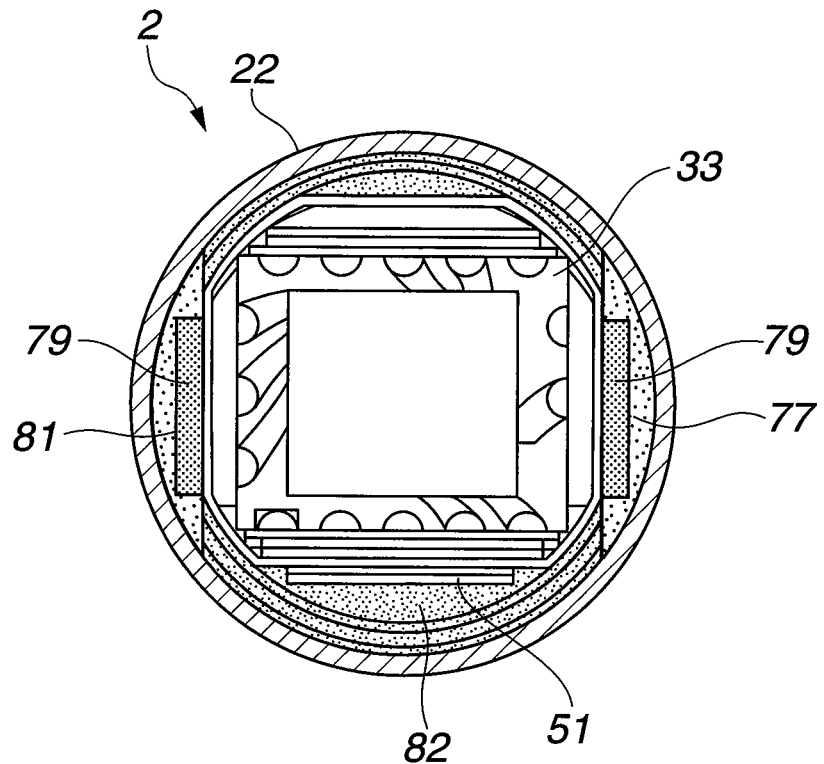
FIG. 8 is a view illustrating the insertion portion shown in FIG. 7, and shows a sectional view that illustrates a modified example of FIG. 6.
Figure 9:
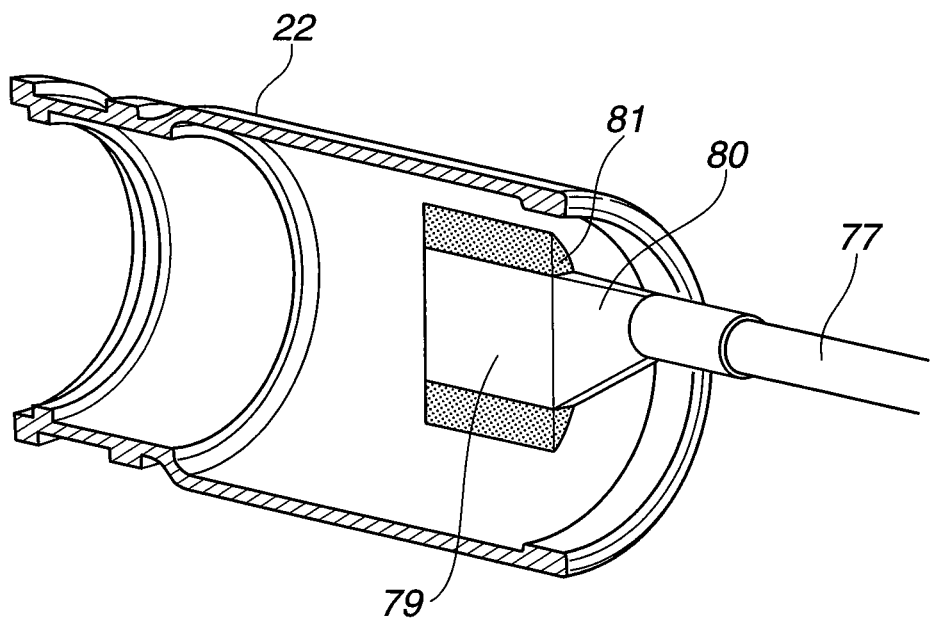
FIG. 9 is an explanatory view illustrating the principal portions of the heat radiating wire element and the distal end cylindrical portion shown in FIG. 8.

As shown in FIG. 7 to FIG. 9, the broad portion 79 of the heat radiating wire element 77 may also be fixed by a solder to the inside peripheral surface of the distal end cylindrical portion 22. Thereby, heat can be conveyed with even better efficiency from the distal end cylindrical portion 22 to the broad portion 79 via a solder portion 81 that generally has a higher thermal conductivity than that of the sealing element 82.

More specifically, a feature of the endoscope apparatus 1 relating to the present invention is that a heat radiating member is fixed by a solder to the inner surface of the distal end portion 2. In the endoscope apparatus 1, since the heat radiating member is fixed by a solder to the inner surface of the distal end portion, heat that is emitted from at least one of the illumination portion and the image pickup portion 23 can be easily released with even better efficiency.

Figure 10:
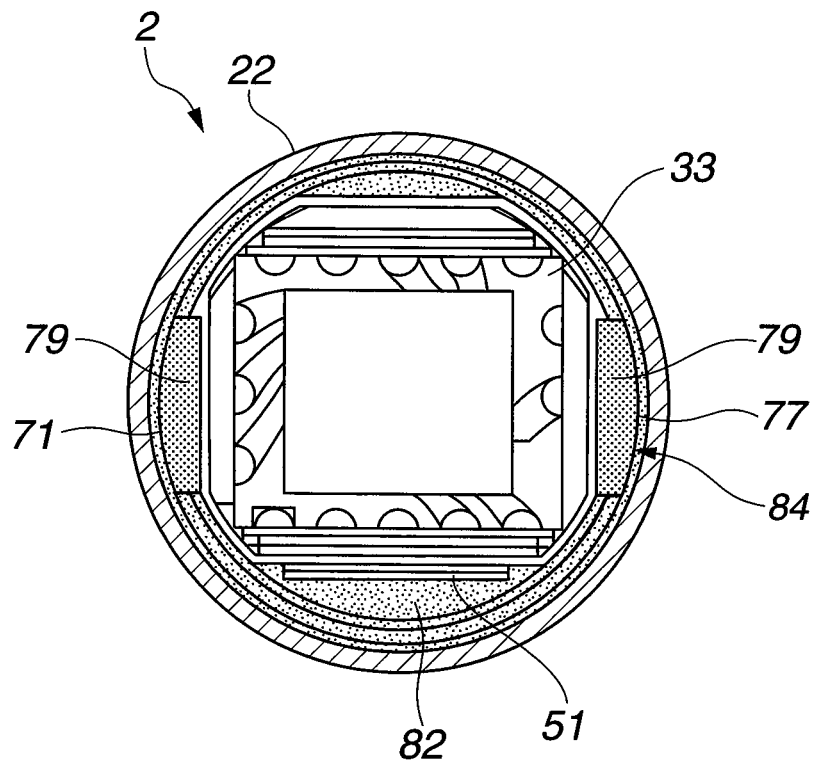
FIG. 10 is a sectional view showing a modified example of FIG. 8.

Further, as shown in FIG. 10, a configuration may be adopted in which one side surface of the broad portion 79 is formed as an arc surface 84 in a shape that protrudes outward. The arc surface 84 is disposed so as to follow the inner surface of the distal end cylindrical portion 22. More specifically, the curvatures of the arc surface 84 and the inner surface of the distal end cylindrical portion 22 are designed to be the same.

In this connection, preferably the arc surface 84 and the inner surface of the distal end cylindrical portion 22 are brought as close as possible, so that the arc surface 84 and the inner surface of the distal end cylindrical portion 22 are made to contact.

By providing the arc surface 84 in this manner, since it is possible to not only increase the heat radiating area of the broad portion 79, but also increase the contact area between the broad portion 79 and the inner surface of the distal end cylindrical portion 22, the heat releasing efficiency can be further improved.

More specifically, a feature of the endoscope apparatus 1 is that the sectional form of the distal end portion 2 is formed in a round shape and the heat radiating member comprises an arc surface that is disposed so as to follow the inner peripheral surface of the distal end portion. Further, in the endoscope apparatus 1, since the heat radiating member comprises an arc surface, the surface area for releasing heat is enlarged. Furthermore, since the arc surface is disposed so as to follow the inner peripheral surface of the distal end portion, heat conveyed to the distal end portion is easily conveyed to the heat radiating member. Thus, in the endoscope apparatus 1, heat emitted from at least one of the illumination portion and the image pickup portion 23 can be easily released with even better efficiency.

Figure 11:
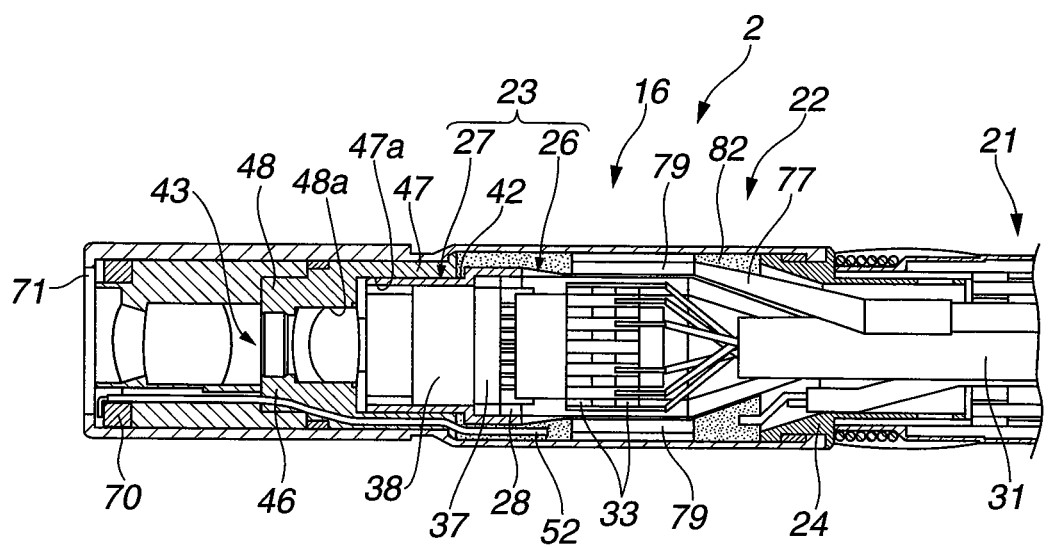
FIG. 11 is a sectional view showing another modified example of the insertion portion shown in FIG. 2.

Although according to the present embodiment, the endoscope adapter 17 is detachably provided in the insertion main body portion 16, the present invention is not limited thereto. For instance, as shown in FIG. 11, the insertion portion 2 may be configured as an integrated unit in which the endoscope adapter 17 is not provided. In this case, the lead 52 is electrically connected to the LED 71. In this case, the distal end cylindrical portion 22 constitutes the distal end portion of the insertion portion 2.

Figure 12:
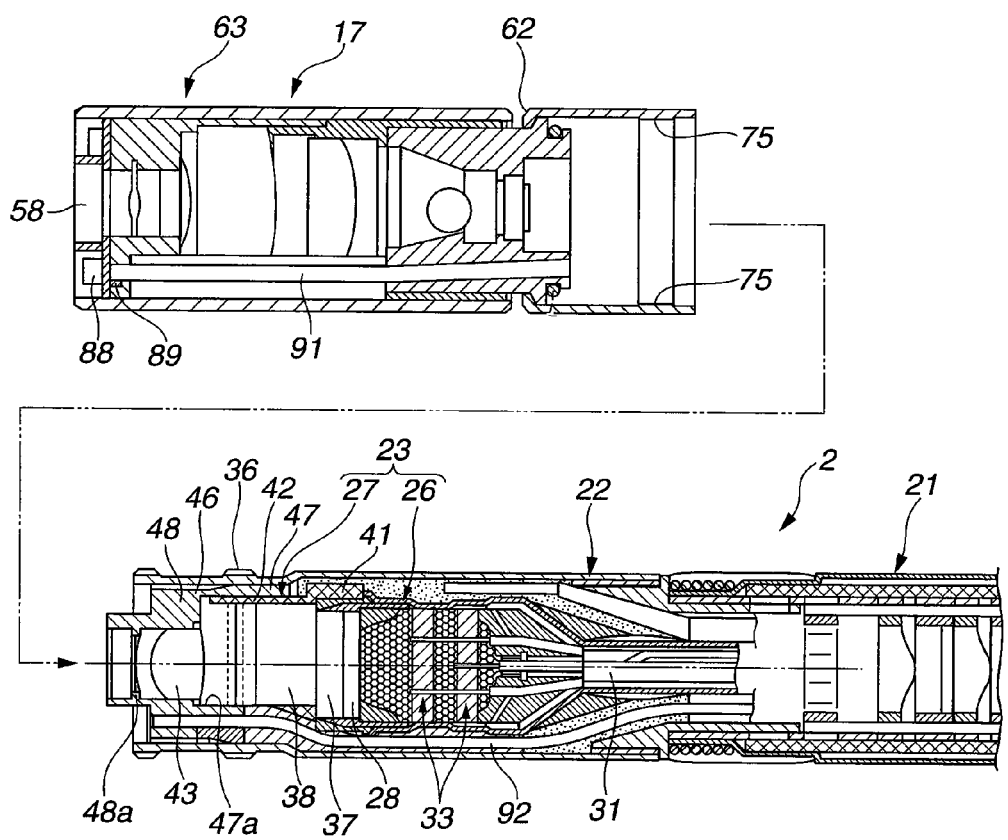
FIG. 12 is a sectional view showing a further another modified example of the insertion portion shown in FIG. 2.

Further, although the LED 71 is provided according to the present embodiment, a configuration may be adopted in which a light source portion is provided in the endoscope main body portion 3 in place of the LED 71, and light from the light source portion is guided by a light guide to be irradiated from the distal end of the insertion portion 2. FIG. 12 is a sectional side view that shows the configuration of the insertion portion 2 in a case in which light is guided by a light guide.

A cover glass for illumination 88 that comprises an illumination portion is provided in the vicinity of the observation window 58. A ball lens 89 that diffuses light from the light source portion so as to correspond to the angle of view is provided at the rear side of the cover glass for illumination 88. An adapter side light guide 91 that extends from the back end surface of the adapter main body portion 63 is also provided at the rear side of the cover glass for illumination 88. The adapter side light guide 91 is configured so as to connect with the insertion portion side light guide 92 provided in the distal end cylindrical portion 22 when the endoscope adapter 17 is attached to the distal end cylindrical portion 22. The insertion portion side light guide 92 is connected to the light source portion provided in the endoscope main body portion 3.

As a result, in comparison to a configuration in which an LED is provided, the generation of heat at the distal end of the insertion portion 2 can be suppressed.

Although the heat-shrinkable tube 80 is provided according to the present embodiment, a normal tube that is not shrunk by heat may be provided in place thereof.

Further, although the sealing element 82 is provided according to the present embodiment, heat can be conveyed to the broad portion 79 from the distal end cylindrical portion 22 and the like even without providing the sealing element 82. However, in that case, naturally the heat conduction efficiency is improved by bringing the broad portion 79 as close as possible to the inner surface of the distal end cylindrical portion 22.

Furthermore, although the maximum external diameter portion is taken as the image pickup cover 41 in the present embodiment, it is possible to suitably change the configuration with respect to which part of the image pickup portion 23 is the maximum external diameter portion.

Further, the endoscope apparatus 1 may have a temperature detection sensor for detecting a temperature at the circumference of the CCD 28. Thus, for example as in the case of an engine inspection immediately after use, when the endoscope apparatus is used under a high temperature environment the temperature of the circumference of a solid image pickup device that is easily affected by heat can be detected and the user is notified of the result so that the temperature of the circumference does not exceed an allowable temperature for properly operating the solid image pickup device.

Further, when a high temperature heat generating component that has a high heating value is provided in the CCD substrate 33, it is possible to release not only the heat from at least one of the illumination portion and the image pickup portion, but also heat emitted from the high temperature heat generating component at the proximal end side of the insertion portion via the sealing element 82 having a high thermal conductivity that is inside the distal end cylindrical portion 22.

In this connection, a plurality of sealing materials of differing thermal conductivities may be used for the sealing element 82 that has a high thermal conductivity inside the distal end cylindrical portion 22. In this case, by providing a sealing material with a higher thermal conductivity on the further proximal end portion side than that of the distal end portion side within the distal end cylindrical portion 22, heat of the insertion portion distal end portion is easily conducted to the proximal end side.

Further, although the endoscope adapter 17 is configured for forward viewing, the present invention is not limited thereto, and the endoscope may be configured as an endoscope for side viewing.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope apparatus, including:
    a long insertion portion that is inserted into an object to be examined;
    an illumination portion that irradiates illumination light at an observation target inside the object to be examined;
    a distal end portion provided at a distal end of the insertion portion and including a cylindrical portion formed in a cylindrical shape;
    an image pickup portion including an image pickup device that photo-electrically converts reflected light which is reflected from the object to be examined, and which is captured in the distal end portion, and a rectangular image pickup substrate portion provided at a rear side of the image pickup device;
    a cover glass arranged at a front of the image pickup device, the cover glass configured to protect a front surface of the image pickup device;
    an image pickup cover formed integrally with the image pickup device of the image pickup portion and the cover glass, for protecting the image pickup device of the image pickup portion and the cover glass;
    a signal wire connected to the image pickup substrate portion of the image pickup portion, the signal wire transmitting an electric signal from the image pickup device and the image pickup substrate portion; and
    a heat radiating member having a first end portion and a second end portion and configured by bundling multiple wire elements made of a high thermal conductivity material, wherein a distal end of the first end portion is arranged on a side of the image pickup substrate portion of the image pickup portion, to be extended to the proximal end side of the insertion portion,
    wherein
    the image pickup portion includes, at a portion where the image pickup cover for protecting the image pickup device is located, a maximum external diameter portion having an external diameter larger than an external diameter of a portion where the image pickup substrate portion is located;
    the signal wire is provided on a more proximal end side than the maximum external diameter portion of the image pickup portion;
    the distal end portion includes four space regions which encircle four outer peripheral surfaces corresponding to respective sides of the rectangular image pickup substrate portion and are positioned between the four outer peripheral surfaces and an inner peripheral surface in the cylindrical portion of the distal end portion, the four space regions formed at a position which is on a more proximal end side than the maximum external diameter portion and which is on a more distal end side than a rear end of the image pickup substrate portion in a state where the image pickup portion is provided in the cylindrical portion of the distal end portion;
    the first end portion of the heat radiating member forms a broad portion which is formed to have a wider width than a portion formed by bundling the wire elements and
    the broad portion of the first end portion is disposed in at least one of the four space regions formed in the distal end portion.

2. The endoscope apparatus according to claim 1, wherein, in the heat radiating member, the distal end of the first end portion is arranged further distal than an image pickup device of the image pickup portion inside the distal end portion.

3. The endoscope apparatus according to claim 1, wherein, in the heat radiating member, a side surface of the broad portion of the first end portion is disposed facing a side surface of the image pickup substrate portion.

4. The endoscope apparatus according to claim 1, wherein the heat radiating member is provided in plural numbers, and the plurality of heat radiating members have respectively different length dimensions.

5. The endoscope apparatus according to claim 4, wherein the second end portions of the plurality of heat radiating members are disposed at respectively different positions with respect to a longitudinal direction of the insertion portion.

6. The endoscope apparatus according to claim 1, wherein a sealing element is filled in the four space regions of the distal end portion, and the sealing element has a high thermal conductivity.

7. The endoscope apparatus according to claim 1, wherein the heat radiating member is fixed by a solder to an inner surface of the distal end portion.

8. The endoscope apparatus according to claim 1, wherein a sectional form of the distal end portion is form in a round shape, and
the heat radiating member comprises an arc surface having a curvature that is the same as a curvature of an inner peripheral surface of the distal end portion.

9. The endoscope apparatus according to claim 1, wherein the illumination portion is provided at the distal end portion of the insertion portion.

10. The endoscope apparatus according to claim 1, wherein the insertion portion includes an insertion portion main body portion and an endoscope adapter that is detachable from the insertion portion main body portion, and
the illumination portion is provided in the endoscope adapter.

11. An endoscope apparatus, including:
a long insertion portion that is inserted into an object to be examined;
a distal end portion provided at a distal end of the insertion portion and including a cylindrical portion formed in a cylindrical shape;
an illumination portion that is provided inside a distal end portion of the insertion portion, and includes an LED that irradiates illumination light at an observation target inside the object to be examined;
an image pickup portion that includes a CCD that photoelectrically converts reflected light which is reflected from the object to be examined and which is captured in the distal end portion, and
a rectangular pickup substrate portion provided at a rear side of the CCD;
a cover glass arranged at a front face of the CCD, the cover glass configured to protect a front surface of the CCD;
an image pickup cover formed integrally with the CCD of the image pickup portion and the cover glass, for protecting the CCD of the image pickup portion and the cover glass;
a signal wire connected to the image pickup substrate portion, the signal wire transmitting an electric signal from the CCD and the image pickup substrate portion; and
a plurality of heat radiating members, each having a first end portion and a second end portion and each being configured by bundling multiple wire elements made of a high thermal conductivity material, wherein a distal end of the first end portion is arranged on a side of the image pickup substrate portion, to be extended to the proximal side of the insertion portion;
wherein:
the image pickup portion includes, at a portion where the image pickup cover for protecting the CCD is located, a maximum external diameter portion having an external diameter larger than an external diameter of a portion where the image pickup substrate portion is located;
the signal wire is provided on a more proximal end side than the maximum external diameter portion of the image pickup portion;
the distal end portion includes four space regions which encircle four outer peripheral surfaces corresponding to respective sides of the rectangular image pickup substrate portion and are positioned between the four outer peripheral surfaces and an inner peripheral surface in the cylindrical portion of the distal end portion, the four space regions being formed at a position which is on a more proximal end side than the maximum external diameter portion and which is on a more distal end side than a rear of the image pickup substrate portion in a state where the image pickup portion is provided in the cylindrical portion of the distal end portion, and
the first end portion of each of the plurality of heat radiating members forms a broad portion which is formed to have a wider width than a portion formed by bundling the wire elements,
the broad portion of the first end portion of each of the plurality of heat radiating member is disposed in at least one of the four space regions formed in the distal end portion; and
the second end portion of each of the plurality of heat radiating members is disposed at a position in the insertion portion which is different from a position of the first end portion of each of the plurality of heat radiating members.

12. The endoscope apparatus according to claim 6, wherein the sealing element fixes the image pickup portion, the heat radiating member, and a distal end side FPC.

13. The endoscope apparatus according to claim 4, wherein regions where the broad portions provided respectively to the plurality of heat radiating members are arranged are two regions opposed to each other so as to sandwich the signal wire and the image pickup portion, among the four regions.

14. The endoscope apparatus according to claim 13, wherein, among the divided four regions, the two regions sandwiching the image pickup portion are regions where the heat radiating members are arranged, and at least another one region is a region where a cable for supplying power to an LED disposed at a further distal end side than the image pickup portion or a light guide for guiding illumination light to a further distal end side than the image pickup portion is arranged.

15. The endoscope apparatus according to claim 6, wherein the sealing element includes different kinds of sealing materials, and is configured such that the sealing material on the proximal end side has higher thermal conductivity than the sealing material on the distal end portion side.

16. The endoscope apparatus according to claim 15, wherein the image pickup substrate portion is provided with a high temperature heat generating component.

17. The endoscope apparatus according to claim 11, wherein regions where the broad portions provided respectively to the plurality of heat radiating members are arranged are two regions opposed to each other so as to sandwich the signal wire and the image pickup portion, among the four regions.

18. The endoscope apparatus according to claim 17, wherein, among the divided four regions, the two regions sandwiching the image pickup portions are regions where the heat radiating members are arranged, and
at least another one region is a region where a cable for supplying power to an LED disposed at a further distal end side than the image pickup portion is arranged.

19. The endoscope apparatus according to claim 11, wherein a sealing element is filled in the divided four regions of the distal end portion, and
the sealing element has a high thermal conductivity.

20. The endoscope apparatus according to claim 19, wherein the sealing element includes different kinds of sealing materials, and is configured such that the sealing material on the proximal end side has higher thermal conductivity than the sealing material on the distal end portion side.

21. The endoscope apparatus according to claim 20, wherein the image pickup substrate portion is provided with a high temperature heat generating component.

22. The endoscope apparatus according to claim 1, wherein two image pickup substrate portions are disposed in parallel with the image pickup device.

23. The endoscope apparatus according to claim 11, wherein two image pickup substrate portions are disposed in parallel with the CCD.

* * * * *

UNITED STATES PATENT AND TRADEMARK OFFICE
CERTIFICATE OF CORRECTION

| | |
|---|---|
| PATENT NO. | : 8,641,606 B2 |
| APPLICATION NO. | : 12/026257 |
| DATED | : February 4, 2014 |
| INVENTOR(S) | : Masaki Ichihashi |

It is certified that error appears in the above-identified patent and that said Letters Patent is hereby corrected as shown below:

Title Page, please insert,

--(73) Assignee:  Olympus Corporation (JP)--

Signed and Sealed this
Fifth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,641,606 B2  
APPLICATION NO. : 12/026257  
DATED : February 4, 2014  
INVENTOR(S) : Masaki Ichihashi Page 1 of 1

It is certified that error appears in the above-identified patent and that said Letters Patent is hereby corrected as shown below:

Title page, item "(76)" should read item -- (75) --.

Title Page, please insert,

-- (73) Assignee:   Olympus Corporation (JP) --.

This certificate supersedes the Certificate of Correction issued August 5, 2014.

Signed and Sealed this  
Ninth Day of September, 2014

Michelle K. Lee  
*Deputy Director of the United States Patent and Trademark Office*